United States Patent [19]
Schneider et al.

[11] Patent Number: 5,900,166
[45] Date of Patent: May 4, 1999

[54] METHOD OF MAKING DEFORMATION TEST SAMPLES OF SOLID SINGLE CRYSTALS

[75] Inventors: Herbert Schneider; Frank Gretschmann, both of Stutensee; Klaus Kickert, Karlsruhe, all of Germany

[73] Assignee: Forschungszentrum Karlsruhe GmbH, Karlsruhe, Germany

[21] Appl. No.: 08/932,767

[22] Filed: Sep. 18, 1997

[30] Foreign Application Priority Data

Dec. 20, 1996 [DE] Germany ............................. 19653458

[51] Int. Cl.⁶ ................................. G01N 1/28; G01N 3/62
[52] U.S. Cl. ............................ 219/69.17; 29/558; 73/863
[58] Field of Search ........................ 219/69.17; 29/558; 73/863

[56] References Cited

U.S. PATENT DOCUMENTS

| 4,404,449 | 9/1983 | Astier et al. | 219/69.2 |
| 4,439,236 | 3/1984 | Ray | 148/334 |
| 4,641,007 | 2/1987 | Lach | 219/69.17 |
| 4,713,516 | 12/1987 | Buhler et al. | 219/69.18 |
| 4,786,776 | 11/1988 | Ramsbro | 219/69.12 |
| 5,061,354 | 10/1991 | Smith et al. | 204/164 |
| 5,833,202 | 11/1998 | Wolfgang | 248/466 |
| 5,837,354 | 11/1998 | Ogisu et al. | 428/208 |

*Primary Examiner*—Thomas P. Noland
*Attorney, Agent, or Firm*—Klaus J. Bach

[57] ABSTRACT

In a method of making deformation test samples of metallic mechanically rigid, single crystals as they are required as sample rods for tension-, compression-, or bending tests in the precision testing of materials, the samples are first generated by known methods as cylindrical raw single crystals having varying diameters and rough surfaces. The raw single crystals are then shaped by wire erosion to provide testing samples of a desired shape and surface quality.

3 Claims, No Drawings

METHOD OF MAKING DEFORMATION TEST SAMPLES OF SOLID SINGLE CRYSTALS

BACKGROUND OF THE INVENTION

The invention relates to a method of making deformation test samples of metallic mechanically rigid single crystals for example for use as sample rods for testing mechanical stress, compression or bending strength of a material in material research.

In material research processes occurring in the interior of metals are preferably examined on single crystals because of the complexity of those processes. The single crystals are produced mainly in accordance with two different manufacturing methods, the method according to Czorchralski and the method according to Bridgeman-Stockbarger. In both cases cylindrical single crystals are obtained which however, cannot be used directly as deformation samples. The Czorchralski crystal has a varying diameter over its length caused by the particular manufacturing method, whereas the Bridgeman-Stockbarger crystal has a sufficiently constant diameter. Since single crystals are very sensitive to deformation, they are destroyed by the slightest bending during handling. For this reason, they cannot be formed to the desired shape. Not even working of the surface of single crystals by forming on a lathe, cutting or drilling or grinding is possible.

It is the object of the present invention to provide a method whereby deformation samples of single crystals such as sample rods can be shaped without being destroyed.

SUMMARY OF THE INVENTION

In a method of making deformation test samples of metallic mechanically rigid, single crystals as they are required as sample rods for tension-, compression-, or bending tests in the precision testing of materials, the samples are first generated by known methods as cylindrical raw single crystals having varying diameters and rough surfaces. The raw single crystals are then shaped by wire erosion to provide testing samples of a desired shape and surface quality.

During working of a sample crystal by spark or wire erosion the sample is preferably first roughly shaped and then subjected to a fine-erosion procedure wherein the surface is smoothened in one or several fine-erosion steps. Further, it is advantageous with a cylindrical base crystal having a varying diameter over its length to cut the crystal in a first wire erosion step down to a constant diameter and then erode it in a subsequent erosion step to the desired shape for the probe sample.

The invention will be described below in greater detail:

The new method permits the manufacture of deformation samples of metallic mechanically rigid single crystals. Such samples generally consist of sample rods of various shapes for tension compression and bending tests and are required for intrinsic tests of materials in metallurgic studies. With the new method, first a cylindrical single crystal is produced which has untreated surfaces with geometric and surface deficiencies as they are inherent to the manufacturing process used. As mentioned earlier, the manufacturing processes available able are the Czorchralski and the Bridgeman processes. Subsequently, the raw crystal is subjected to spark or wire erosion to form it to the desired shape. During this treatment of spark or wire erosion, first the rough shape of the sample is provided with relatively large material removal and then the surface is smoothened by one or several fine-erosion steps. All sample shapes, for example proportional rods, can be produce in accordance with industrial standards such as DIN. With this method, also optimized rectangular samples or other shapes can be provided by pattern erosion using a template. Also, the manufacture of flat tension samples is possible.

Important for the invention is however the spark erosion procedure. Spark erosion is a contact-free material removal process wherein, by electric discharges in an operating gap between the surface to he worked and an electrode, material is removed from the surface. The parameters responsible for the amount of material removal are the impulse frequency, the discharge charge energy and the width of the gap. With a high impulse frequency, a low discharge density and a small spark gap the amount of material removal is relatively small and the surface generated is relatively smooth. Correspondingly, with a low impulse frequency, a high discharge energy and a large spark gap, a relatively large amount of material is removed from the surface while a relatively rough surface is generated. The greatest influence on what happens in the spark gap has the discharge energy $W_e$:

$$W_e = u_e \times t_e \times i_e$$

This is the energy amount converted in the spark gap during the discharge. It corresponds to the product of the average discharge voltage $u_e$, the average discharge current $i_e$ and the discharge duration $t_e$.

First, in a first step, a first cylindrical base crystal is produced according to the method of Czorchralski, which crystal has a varying diameter over its length. This crystal is then cut down to a constant diameter by wire erosion as mentioned earlier, and is finally eroded in a second step to the desired final sample shape. The amount of the material being removed determines the surface quality of the deformation sample so produced. During erosion of the single crystal to generate the deformation sample, first the sample is formed to a rough shape by removing a relatively large amount of material and the surface is then smoothened by a number of fine-erosion steps as mentioned earlier. For obtaining a good quality surface, the quality of the fine-erosion must be good. It is possible without any problems to obtain a surface with a roughness of less than 1 $\mu$m. with such a smooth surface, there are no cutting ridges on the sample surface which could form starting points for microcracks.

DESCRIPTION OF EXAMPLES

Below two examples for the production of deformation samples in accordance with the present invention are presented.

Example 1

Cu single crystal (EK)

| | |
|---|---|
| Original diameter | 8–10 mm |
| Length | 80 mm |
| Orientation | random |

Type of the deformation sample: measuring length square, end sections baud curve to avoid tension peaks.

Cutting sequence:

1. main cut:
    wire 0.25 mm diameter   v = 2.0 mm/min
1. Precision cut:
    wire 0.15 mm diameter   v = 1.5 mm/min
2. precision cut:
    wire 0.10 mm diameter   v = 1.0 mm/min Example 2
Cu EK (EK according to Czorchaiski):

| Original diameter | 8 to 10 mm |
|---|---|
| Length | 100 mm |
| Orientation | random |

Type of deformation sample: measuring length square, end sections band curve to avoid tension peaks.
Cutting sequence:

1. main cut:
    wire            0.25 mm diameter   v = 2.5 mm/min
1. precision cut:
    wire            0.15 mm diameter   v = 1.5 mm/min
2. precision cut:
    wire            0.15 mm diameter   v = 1.0 mm/min The cutting and advancement values as well as the wire diameter and the cutting material are different depending on the single crystal material being cut. The shape of the end sections in the form of a Baud curve is chosen because of the test procedure; but any shape or radius of curvature which is in accordance with given standards could be utilized for making the deformation samples. Generally, with the given method, smaller wire diameters and smaller gaps provide for greater surface qualities. Also, the number of precision cuts can be increased for improving the surface quality.

What is claimed is:

1. A method of making deformation test samples of metallic mechanically rigid single crystals as they are required as sample rods for tension-, compression-, and bending tests in the precision testing of materials in metallurgical test procedures, comprising the steps of:

a) providing a cylindrical single raw crystal with a rough surface having a shape and surface depending on the manufacturing method, and b) subjecting the raw single crystal to spark or wire erosion to produce the desired shape and surface quality.

2. A method according to claim 1, wherein said raw single crystal is first shaped by spark or wire erosion with a high material removal rate to roughly shape the sample and then surfaces are smoothened by at least one fine erosion step.

3. A method according to claim 1, wherein in step a) a cylindrical base crystal with varying diameter is provided and said base crystal, in a first step, is cut to a constant diameter over its length by wire erosion and is then in another step eroded to the desired final sample shape.

* * * * *